United States Patent [19]

Yang

[11] Patent Number: 4,532,797

[45] Date of Patent: Aug. 6, 1985

[54] INSTRUMENTATION FOR SENSING MOISTURE CONTENT OF MATERIAL USING A TRANSIENT THERMAL PULSE

[75] Inventor: Lien C. Yang, La Canada, Calif.

[73] Assignee: The United States of America as represented by the Administrator of the National Aeronautics and Space Administration, Washington, D.C.

[21] Appl. No.: 563,890

[22] Filed: Dec. 22, 1983

Related U.S. Application Data

[63] Continuation of Ser. No. 325,885, Nov. 30, 1981, abandoned.

[51] Int. Cl.$^3$ .............................................. G01N 25/56

[52] U.S. Cl. ........................................ 73/75; 324/65 P

[58] Field of Search ............................ 73/75, 73, 204; 324/65 P; 338/34

[56] References Cited

U.S. PATENT DOCUMENTS

| | | | |
|---|---|---|---|
| 2,343,520 | 3/1944 | Baver | 73/75 |
| 3,246,216 | 4/1966 | Mead | 73/73 |
| 3,517,549 | 6/1970 | Teich | 73/73 |
| 3,782,179 | 1/1974 | Richards | 73/73 |
| 3,813,927 | 6/1974 | Furgason | 73/73 |
| 4,043,196 | 8/1977 | Trageser | 73/204 |

FOREIGN PATENT DOCUMENTS

| | | | |
|---|---|---|---|
| 1179721 | 5/1959 | France | 324/65 P |
| 579255 | 8/1958 | Italy | 324/65 P |

*Primary Examiner*—Charles Frankfort
*Assistant Examiner*—Denis E. Corr
*Attorney, Agent, or Firm*—Paul F. McCaul; John R. Manning; Thomas H. Jones

[57] ABSTRACT

Instrumentation for sensing moisture content of material using a transient thermal pulse is comprised of a sensing probe (12) having a sensing element (14) in the form of a ribbon excited by a constant current pulse from a source (16) to increase the temperature, and therefore the resistance, of the ribbon linearly. Moisture in web material (10) will limit the increase of temperature during the pulse in proportion to the moisture content. This increase in temperature produces a proportional increase in resistivity which is measured with a Wheatstone bridge ($R_1$, $R_2$, $R_3$, 14) as a change in voltage displayed by a measurement display unit (20). The probe (12) is glued in a shallow groove of a Lucite bar (15*c*) and connected to copper pins (15*a*, 15*b*) embedded in the bar. A cylindrical Lucite block (21) may be used to hold the sensing element (14) connected to axial pins (22*a*, 22*b*) in order for the probe to roll and thus reduce its wear.

10 Claims, 5 Drawing Figures

CONSTANT CURRENT PULSE SOURCE
16
R2
R3
R1
I
E
E
I
18
MEASUREMENT DISPLAY UNIT
20
12
15c
15b
15c
10
14

INSTRUMENTATION FOR SENSING MOISTURE CONTENT OF MATERIAL USING A TRANSIENT THERMAL PULSE

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

This application is a continuation of application Ser. No. 325,385, filed 11/30/81, now abandoned.

BACKGROUND OF THE INVENTION

This invention relates to instrumentation for measuring the moisture content of material, particularly moving web material by using a transient thermal pulse.

In many industries, such as in the production of paper and textiles, drying of water in a web is part of the process. Due to the large heat of vaporization required for drying of water, large quantities of energy are consumed. Recent studies indicate that this is an area in which significant energy conservation can be achieved if the efficiency of the drying process can be optimized by precise measurement and control.

Currently available commercial instruments have a number of disadvantages which limit their widespread use. Most are too expensive, particularly for small business establishments having limited capital. This is particularly true of some instrumentation techniques, such as infra-red, neutron and microwave moisture sensing. They involve investments of $5000 to $20,000, or more.

Another disadvantage is the lack of an automated readout which would make possible feedback control of the process. The popular dew point instruments provide only temperature readings. Conversion to relative humidity requires an operator to make reference to a psychrometric table. In addition these instruments cannot be used for automated process control because no convenient electrical signal is produced which would be used for the purpose. This fault is also present in the class of moisture sensors which operate on mechanical principles.

Most of the available moisture sensing instruments, such as the hygroscopic chemical-resistance type sensors, do not have a linear response. This disadvantage necessitates the use of sophisticated electronics to compensate for the nonlinearity. Another limitation is slow response. It is not uncommon for moisture sensing systems to require stabilization times on the order of more than 30 seconds to several minutes.

Yet another limitation is the size of the head of available instruments which contain the probe. Large probe heads are inconvenient for installation due to the large size of the instrumentation package.

Instruments requiring air sampling for reference are also inconvenient. The lack of environmental stability is another disadvantage. Hygroscopic chemical and ion-exchange-resin type resistance probes usually deteriorate with time when exposed to contaminants, such as smoke and certain chemicals. This affects calibration which leads to inaccurate control. Calibration is difficult with many instruments.

Periodic recalibration is essential to insure repeatable results. Only a small number of instruments make provision for this, and in most cases the instrument probe must be dismounted and placed in a humidity controlled chamber for comparison with a standard.

The disadvantages are largely responsible for the limited use of moisture sensing systems in processing. Any instrumentation which minimizes or eliminates such disadvantages would therefore be of great interest.

SUMMARY OF THE INVENTION

In accordance with the present invention, a sensing element comprised of a thermally and electrically conductive thin ribbon is excited by pulses of constant current. The Joule heating which takes place during the pulse raises the element temperature above the ambient temperature and changes its resistance linearly. Contact with a moist material produces better heat transfer from the element is compared to air, thus limiting its temperature in relation to moisture content, thereby causing a different amount of resistance change of the element during the pulse. By monitoring the ribbon resistance during the application of the pulse, such as by the use of a Wheatstone bridge connected to an oscilloscope, or other means for displaying the element resistance as a function of time, the moisture in the material can be determined. In the case of the material being in the form of a moving web, such as in a paper or textile mill, the element is periodically pulsed and the resistance is continually monitored to determine the moisture content of the web, thus making possible feedback control of the drying process.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
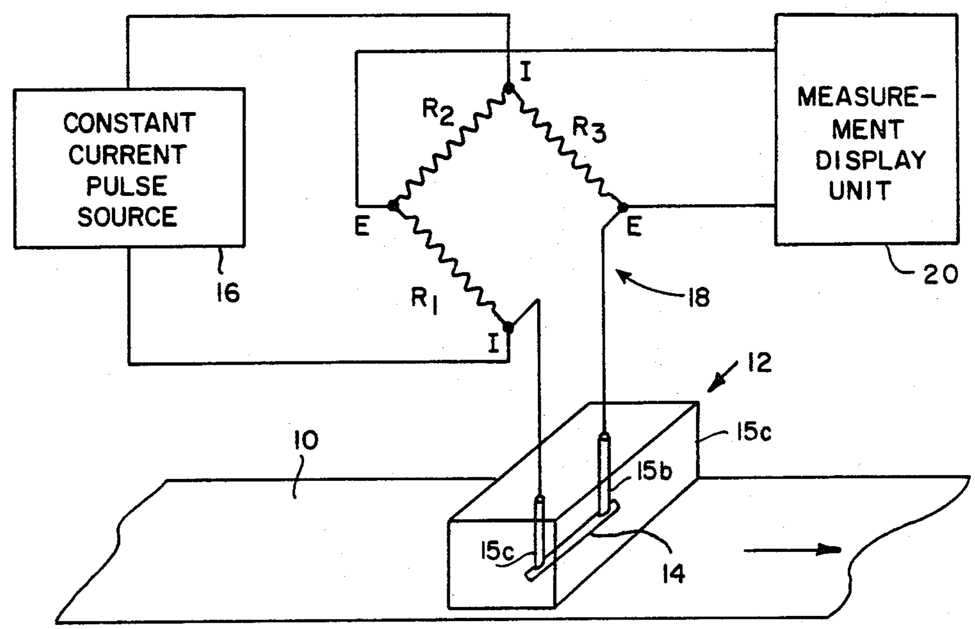
FIG. 1 is a schematic diagram illustrating the present invention.

Referring now to FIG. 1 of the drawings, instrumentation is disclosed for measuring the moisture content of a moving web 10 of paper, textile or the like, using a transient thermal pulse technique. The instrumentation employs a probe 12 having a sensing element 14 which is both thermally and electrically conductive. This element is mounted on the lower face of the probe 12 so that it may be in contact with the web 10 for sensing the moisture content of this web.

The sensing element 14 is periodically excited by a pulse of constant current from a source 16. Such a pulse is shown in waveform A of FIG. 2. The Joule heating by each current pulse of the sensing element in the atmosphere raises its temperature, $\Delta T$, above the ambient temperature and increases its resistance proportionally, as shown by the dashed-line waveform B in FIG. 2. Contact with the moist web 10 produces heat transfer from the sensing element, thereby reducing its temperature rise, as shown by the solid-line waveform B in FIG. 2. That in turn causes a reduced increase of resistance of the sensing element proportional to the change in temperature, $\Delta T$. The change in resistance of the sensing element 14 is then measured as a change in voltage, $\Delta E$, across the element in a Wheatstone bridge 18 comprised of resistors $R_1$, $R_2$ and $R_3$.

Figure 2:
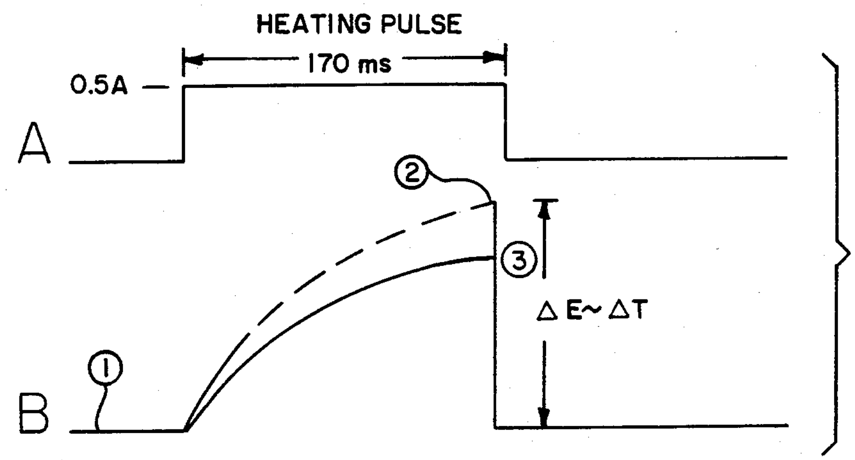
FIG. 2 is a diagram of current and voltage pulse waveforms for the transient thermal pulse technique used in the invention.

By measuring the initial resistance of the sensing element, i.e., the voltage at point 1 in FIG. 2 before application of the current pulse, again at the end of each pulse before contact with the web, which is at point 2 in FIG. 2, and finally at the end of each pulse after contact with the web, shown as point 3 in FIG. 2, data is obtained that can be utilized to determine the amount of moisture in the web. This fact is used to provide on-line measurement of moisture content for feedback control of some part of the web drying process.

Most metals exhibit an increase in resistance with temperature which is linear over some useful range. Alloys usually exhibit a smaller increase, i.e., exhibit a smaller temperature coefficient than pure metals, again over some useful range. Change of the physical character of the metal can also cause a change in its temperature coefficient. Consequently, the choice of metal will depend not only on the range of temperature desired, but also any physical change in the character of the metal used for the sensing element that may occur during assembly of the probe.

The resistance variation of the sensing element can be measured in any of the usual ways known to those skilled in the art. For example, the element can be used as just a resistance-thermometer element with separate voltage (E) and current (I) terminals connected to the ends of the elements, but the more common way is with a Wheatstone bridge arrangement shown in FIG. 1. The bridge is balanced by adjusting resistor $R_1$, $R_2$ or $R_3$ for the initial temperature of the element. Any change in the temperature of the element due to energy applied through current terminals unbalances the bridge across the voltage terminals, causing the appearance of a voltage at a measurement display unit 20, such as an oscilloscope or any analog or digital recording device synchronized by the current pulse to display the waveform B of FIG. 2.

It should be noted that if the current pulses are periodic square-wave pulses, the output between the voltage terminals is an alternating current signal of an amplitude which varies as a function of the resistance of the sensing element. Consequently, it would not be necessary to measure the peak change in temperature on a pulse by pulse basis for continually monitoring the moisture of the web 12. Instead the amplitude of the continuous AC output could be compared with a reference for a desired moisture content. Any differences between the output and the reference can then be used as an error feedback to the system for the drying process.

Figure 3:
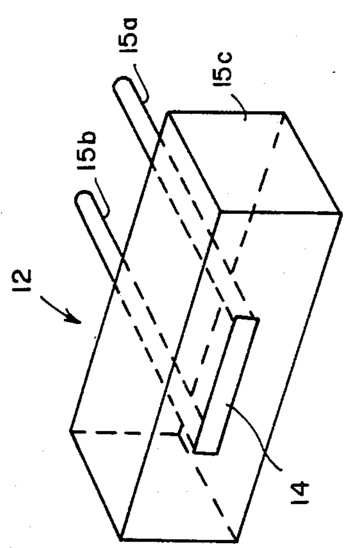
FIG. 3 is an isometric view of the bottom of the moisture sensing probe illustrated in FIG. 1.
Figure 5:
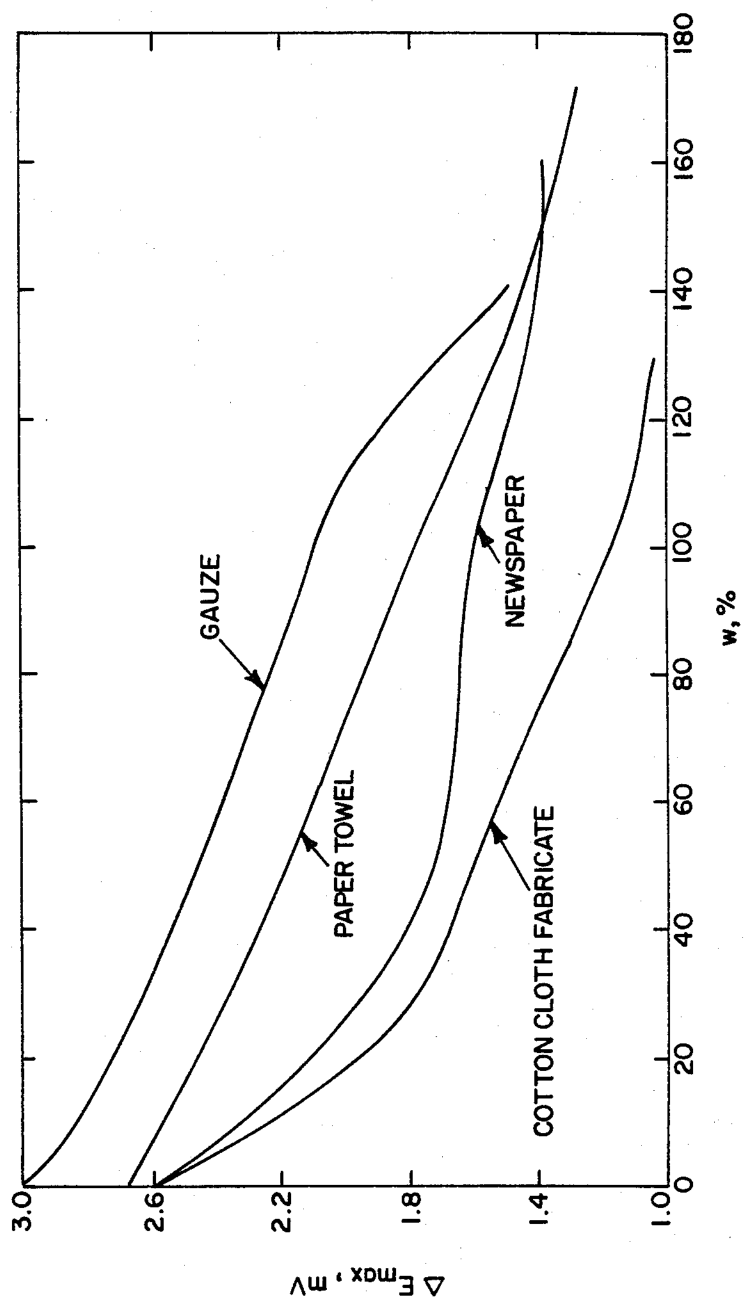
FIG. 5 is a graph of voltage pulse amplitude as a function of moisture content for various web materials.

The present invention was tested by fabricating a probe as shown in FIG. 3. The sensing element 14 was made from type 304 stainless steel foil 12.7 μm (0.0005 inch) thick,, 2.54 cm (1 inch) long and 1.14 mm (0.045 inch) wide. This element has a resistance of about one ohm at ambient temperature (23° C.). The element was soldered at its ends to two copper pins 15*a*, 15 *b* for making electrical connection, and glued into a shallow groove in a Lucite bar 15*c*, flush with the surface bar to protect the element against wear by the moving web 10.

Figure 4:
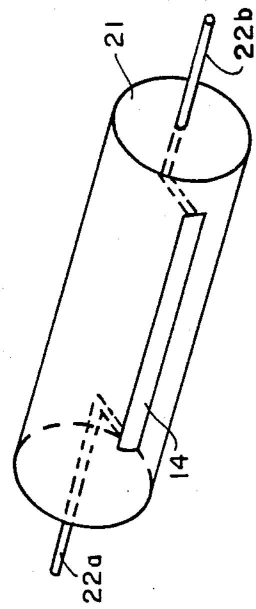
FIG. 4 is an isometric view of a roller-type moisture sensing probe for use in the present invention.

A roller-type probe shown in FIG. 4 could be used to further reduce wear. There a cylindrical Lucite block 21 would be prepared with a groove to receive the sensing element 14 flush with the surface, and the ends of the element would be connected to rotary connectors 22*a* and 22*b*. As the web moves, the roller-type probe would turn, and while the element 14 is in contact with the web 10, it would be pulsed. The pulse could be automatically triggered by sensing the temperature difference between the web and the ambient.

For testing the arrangement of FIG. 1, a sample of web material was placed on a Lucite plate and the probe was laid upon the sample with the sensor element 14 in contact with the sample surface. A weight was placed on the sensor so that a constant contact pressure could be maintained between the sensor element and the material under test, but it was found that the probe was insensitive to contact pressure.

A square wave having a constant current amplitude of 0.5 A was found to be the minimum workable level, for the probe design under test. A Wheatstone bridge type of transient testing instrument (Model 605, Pasadena Scientific Industries, Inc. developed for bridgewire testing) was used in conjunction with an oscilloscope. The square-wave pulses had a duration of 170 msec, although it was found that pulse duration did not significantly affect results. After the bridge was nulled to cancel any DC offset, the extracted AC signal produced by the change of resistance was displayed on the oscilloscope. Waveform B of FIG. 2 shows a typical trace which was obtained.

Several common materials such as a paper towel, newsprint, cotton cloth and gauze were tested. Each sample was soaked in water and allowed to dry slowly in air. Water content was determined by acurate weighting of the samples before soaking and just prior to testing. The data obtained in the testing are shown in FIG. 6, with the maximum amplitude of the AC signal plotted against the percentage of water. This test demonstrates there is a definite correlation between the probe output and the moisture content of the sample, but in order to achieve repeatable results, calibration of the instrumentation for each web material is required. However, calibration may be easily carried out at the paper or textile mill.

Although particular embodiments of the invention have been described and illustrated herein, it is recognized that modifications and variations may readily occur to those skilled in the art. For example, the sensing element may be made from a material having a negative temperature coefficient of resistance instead of a positive one. Consequently it is intended that the claims be interpreted to cover such modifications and equivalents.

What is claimed is:

1. A transient method of measuring the moisture content of material using a short current pulse through a sensor having an element that is thermally and electrically conductive, the resistance of which varies as a function of its temperature, comprised of determining the resistance of said element on application of a short pulse of constant current energy, placing said element in thermal contact with said material, heating said element with said short pulse of constant current energy, determining the peak change in resistance of said element during the application of said short pulse of current while said element is in contact with said material and always previous to any thermal equilibrium that would be reached by said element while in contact with said material, said peak change being a measure of moisture content of said material.

2. A transient method of measuring the moisture content of material using a short current pulse through a thermally and electrically conductive sensor element the resistance of which varies in proportion to its temperature, comprising the steps of measuring the resistance of said sensing element at ambient temperature, placing said element in thermal contact with said material, heating said element with constant current pulse, thereby to raise its temperature, said constant current pulse having a duration in the order of milliseconds, determining the resistance of said element at the peak of its raised temperature during the presence of said constant current pulse and always previous to any thermal equilibrium that would be reached by said element while in contact with said material, and correlating the measured resistances of said element with moisture content of said material.

3. A method as defined in claim 2 wherein the step of correlating the measured resistance is by use of a graph of experimental data for said material over a desired range of moisture content.

4. A method as defined in claim 3 wherein resistance is determined as a voltage across said element while said constant current pulse is being applied, and said experimental data is a graph of change in peak voltage as a function of moisture content.

5. A method as defined in claim 1 wherein said element is periodically pulsed with constant current pulses, and resistance of said element during each pulse period is determined as a voltage across said element, whereby an alternating current signal is derived from said element having an amplitude proportional to moisture content for continually monitoring the moisture content of said material.

6. Apparatus for sensing the moisture content of material using a short current pulse comprising a sensor adopted to be in thermal contact with said material, said sensor having a thermally and electrically conductive element the resistance of which varies in proportion to its temperature, means for pulsing said element at the time the moisture content is to be sensed with a constant current pulse, said pulse having a duration in the order of milliseconds, and means for determining said change in resistance achieved in said element in response to each pulse of constant current, always previous to reaching any thermal equilibrium as a measure of moisture content of said material.

7. Apparatus as defined in claim 6 wherein said sensor is comprised of a thin ribbon of metal and means for placing said ribbon in thermal contact with said material.

8. Apparatus as defined in claim 7 wherein said means for placing said ribbon in thermal contact with said material is comprised of a body of material that is not an electrical conductor and is a poor thermal conductor.

9. Apparatus as defined in claim 8 wherein said body is a bar and said ribbon is mounted in a groove on one face of said body flush with the surface thereof, and electrical conductors are connected to ends of said ribbon through said body.

10. Apparatus as defined in claim 8 wherein said body is a cylinder and said ribbon is mounted in a groove parallel to the axis of said cylindrical body flush with the surface thereof, and electrical conductors are connected to ends of said ribbon through axial rotary connectors extending into ends of said body, whereby said body may roll on said material in response to relative motion between said body and said material the moisture content of which is being measured.

* * * * *